US008882879B2

(12) United States Patent
Hsu et al.

(10) Patent No.: US 8,882,879 B2
(45) Date of Patent: Nov. 11, 2014

(54) METHOD FOR PREPARING NANO SILVER PARTICLES

(75) Inventors: Tsung-Ju Hsu, Taichung (TW); An-Ting Kuo, New Taipei (TW)

(73) Assignee: BenQ Materials Corporation, Taoyuan County (TW)

( * ) Notice: Subject to any disclaimer, the term of this patent is extended or adjusted under 35 U.S.C. 154(b) by 294 days.

(21) Appl. No.: 13/365,276

(22) Filed: Feb. 3, 2012

(65) Prior Publication Data

US 2013/0008287 A1    Jan. 10, 2013

(30) Foreign Application Priority Data

Jul. 8, 2011   (TW) .............................. 100124179 A

(51) Int. Cl.
| | |
|---|---|
| *B22F 9/24* | (2006.01) |
| *B82Y 40/00* | (2011.01) |
| *B22F 1/00* | (2006.01) |
| *B82Y 30/00* | (2011.01) |
| *A01N 59/16* | (2006.01) |

(52) U.S. Cl.
CPC ................. *B22F 1/0018* (2013.01); *B22F 9/24* (2013.01); *B82Y 30/00* (2013.01); *B82Y 40/00* (2013.01); *A01N 59/16* (2013.01); *Y10S 977/896* (2013.01)
USPC ............................................ 75/371; 977/896

(58) Field of Classification Search
None
See application file for complete search history.

(56) References Cited

U.S. PATENT DOCUMENTS

| | | | |
|---|---|---|---|
| 5,759,230 A | 6/1998 | Chow et al. | |
| 7,270,694 B2 | 9/2007 | Li et al. | |
| 7,585,349 B2 * | 9/2009 | Xia et al. ........................ | 75/371 |
| 7,591,872 B1 | 9/2009 | Jun et al. | |
| 2006/0065075 A1 | 3/2006 | Chang et al. | |
| 2006/0115536 A1 | 6/2006 | Yacaman et al. | |
| 2008/0210052 A1 * | 9/2008 | Allemand ....................... | 75/300 |
| 2009/0130433 A1 * | 5/2009 | Takada .......................... | 428/328 |
| 2009/0214766 A1 * | 8/2009 | Magdassi et al. ............. | 427/125 |
| 2010/0189901 A1 | 7/2010 | Chung et al. | |
| 2010/0203333 A1 | 8/2010 | Mokhtari et al. | |
| 2010/0224026 A1 | 9/2010 | Brennan Fournet et al. | |
| 2011/0313059 A1 * | 12/2011 | Blosi et al. ...................... | 516/97 |

OTHER PUBLICATIONS

Machine translation of CN-101869988-A, published Oct. 27, 2010.*

* cited by examiner

*Primary Examiner* — George Wyszomierski
(74) *Attorney, Agent, or Firm* — CKC & Partners Co., Ltd.

(57) ABSTRACT

The invention provides a method for preparing nano silver particles comprising mixing polyvinyl pyrrolidone (PVP) and silver nitrate ($AgNO_3$) in a solvent to form a reactive solution, heating the reactive solution to a temperature less than the boiling point of the solvent for the formation reaction of nano silver particles, adding an accelerating agent into the reactive solution during the formation reaction of the nano silver particles, and terminating the formation reaction when the size of the nano silver particles formed in the reaction solution reaches about 50 nm to 120 nm in diameter.

10 Claims, 12 Drawing Sheets

METHOD FOR PREPARING NANO SILVER PARTICLES

CROSS-REFERENCE TO RELATED APPLICATION

This application claims the priority benefit of Taiwan application serial no. 100124179, filed on Jul. 8, 2011, the full disclosure of which is incorporated herein by reference.

BACKGROUND

1. Technical Field

The invention relates to a method for preparing nano silver particles. More particularly, the invention relates to a method for preparing nano silver particles with a particle size of 50 nm to 120 nm, in which the method is suitable for use in mass production of nano silver particles.

2. Description of Related Art

Since nano silver particles possess strong oxidant capacity to resist bacteria and viruses, they have shown great anti-bacterial and anti-virus effects and have become a popular topic of research in various fields. For example, much research is being conducted in the area of coating anti-bacterial materials with nano silver particles.

However, it is suggested in recent research that nano silver particles with a particle size smaller than 30 um would induce a serious bio-toxic effect on the human body and beneficial bacteria existing in nature. Therefore, the safety of nano silver particles with a small particle size has attracted much attention all over the world.

Generally, silver metal formed by a nanofabrication process may be referred to as nano silver particles. However, nano silver particles prepared by a conventional mechanical grinding method only reach about 500 nm in diameter and such a method has a serious problem with particle size control. Therefore, the chemical reduction method for preparing silver nano particles is significantly desired. The chemical reduction method involves adding a reduction to agent into silver nitrate solutions to make silver ion in the solutions gain an electron to be reduced to silver with a specific nano particle size as necessary. However, the particle size of the nano silver particles manufactured by the IPA system is about 20 nm or less and the particles in this size would induce a serious bio-toxic effect on the human body and beneficial bacteria existing in the nature. As a result, in order to overcome the disadvantages of the method mentioned above, a method for preparing nano silver particles with a particle size larger than 30 nm is desired.

SUMMARY

In accordance with an aspect of the present invention, a method for preparing nano silver particles with a particle size of 50 nm to 120 nm is provided. The method comprises mixing polyvinyl pyrrolidone (PVP) and silver nitrate ($AgNO_3$) in a solvent to form a reactive solution, heating the reactive solution to a temperature less than the boiling point of the solvent for the formation reaction of nano silver particles, adding an accelerating agent into the reactive solution during the formation reaction of the nano silver particles, and terminating the formation reaction when the size of the nano silver particles formed in the reaction solution reaches about 50 nm to 120 nm.

According to another aspect of the present invention, the solvent is selected from the group consisting of isopropyl alcohol (IPA), $H_2O$ and a combination thereof.

According to yet another aspect of the present invention, the temperature is to in a range of 60° C. to 80° C.

According to yet another aspect of the present invention, the reaction time for formation of the nano silver particles is from 5 hours to 50 hours.

According to yet another aspect of the present invention, the accelerating agent is selected from the group consisting of glucose, amine, Sodium hydroxide (NaOH), Potassium hydroxide (KOH), Hydrogen ($H_2$) and a combination thereof.

According to yet another aspect of the present invention, the molar ratio of the PVP to the solvent is 0.012 to 0.032 and the molar ratio of the $AgNO_3$ to the PVP is 0.5 to 1.5.

According to yet another aspect of the present invention, when $H_2$ is used as the accelerating agent, $H_2$ is added into the reactive solution before the reactive solution is heated.

According to yet another aspect of the present invention, when $H_2$ is used as the accelerating agent, the addition of $H_2$ into the reactive solution is discontinued after the reactive solution is heated for 6 hours to 20 hours.

According to yet another aspect of the present invention, the reactive solution is cooled to room temperature after the addition of $H_2$ into the reactive solution is discontinued and the formation reaction is conducted for another 10 hours to 20 hours.

The above and other aspects of the invention will become better understood with regard to the following detailed description of the preferred but non-limiting embodiment(s). The following description is made with reference to the accompanying drawings.

DETAILED DESCRIPTION

Figure 1A:
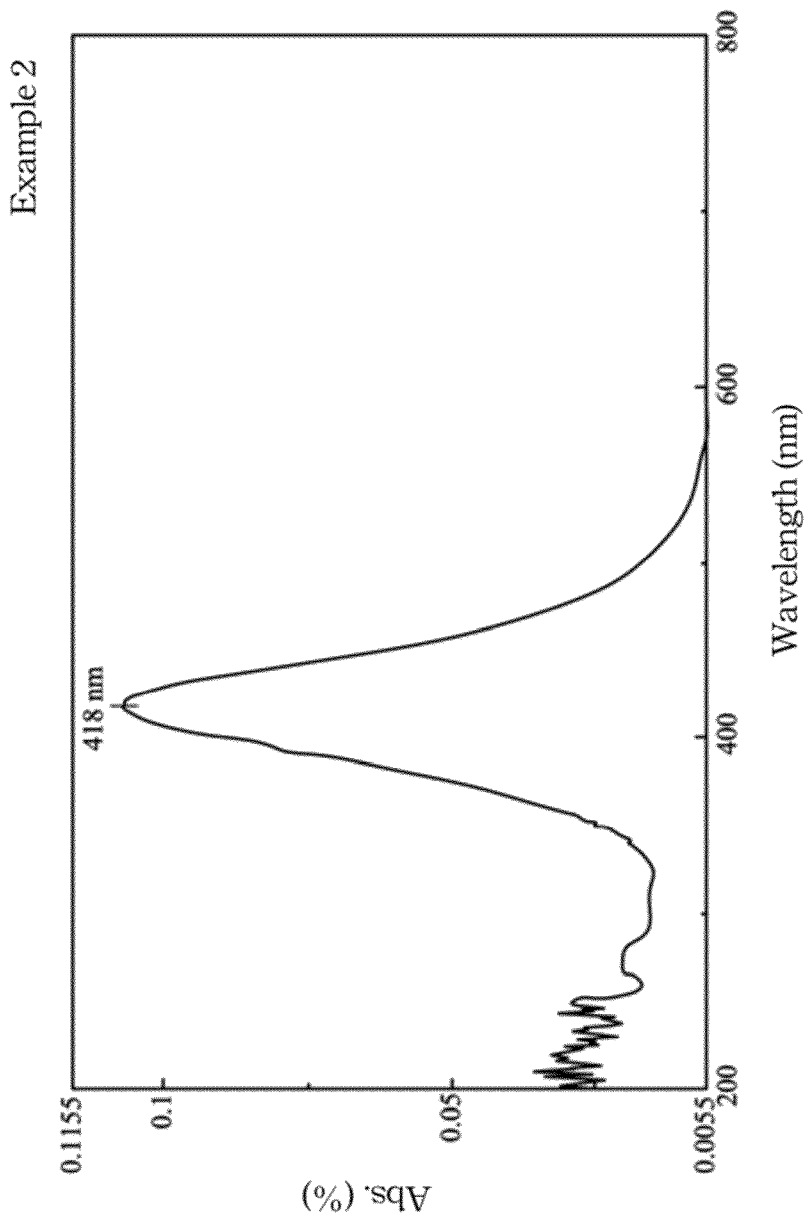
FIG. 1a is the UV-Vis spectrum of a reactive solution of Example 2 after a reaction time of 26 hrs.
Figure 1B:
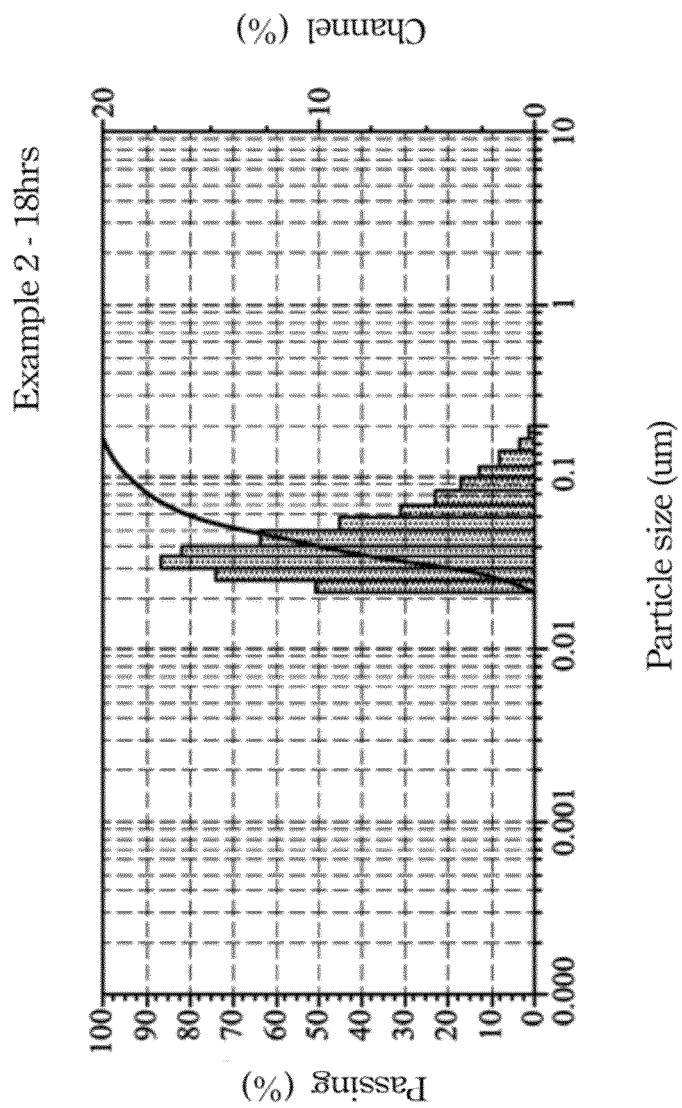
FIGS. 1b to 1f are nano silver particle size distribution curves of the is reactive solution of Example 2 after reaction times of 18 hrs, 26 hrs, 40 hrs, 46 hrs and 49 hrs.
Figure 1C:
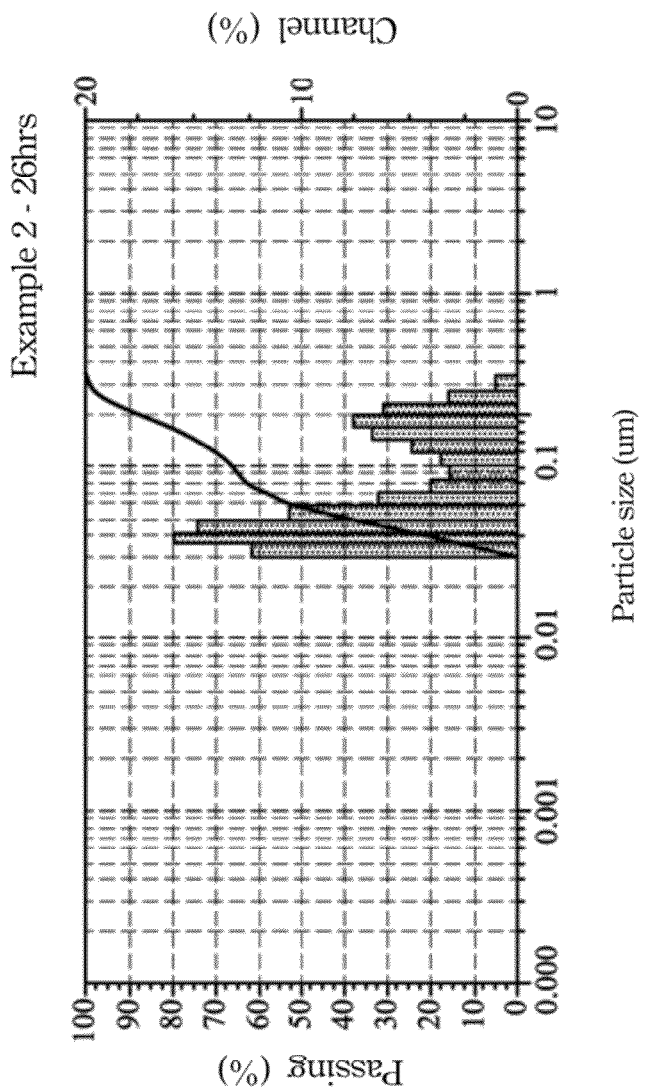
Figure 1D:
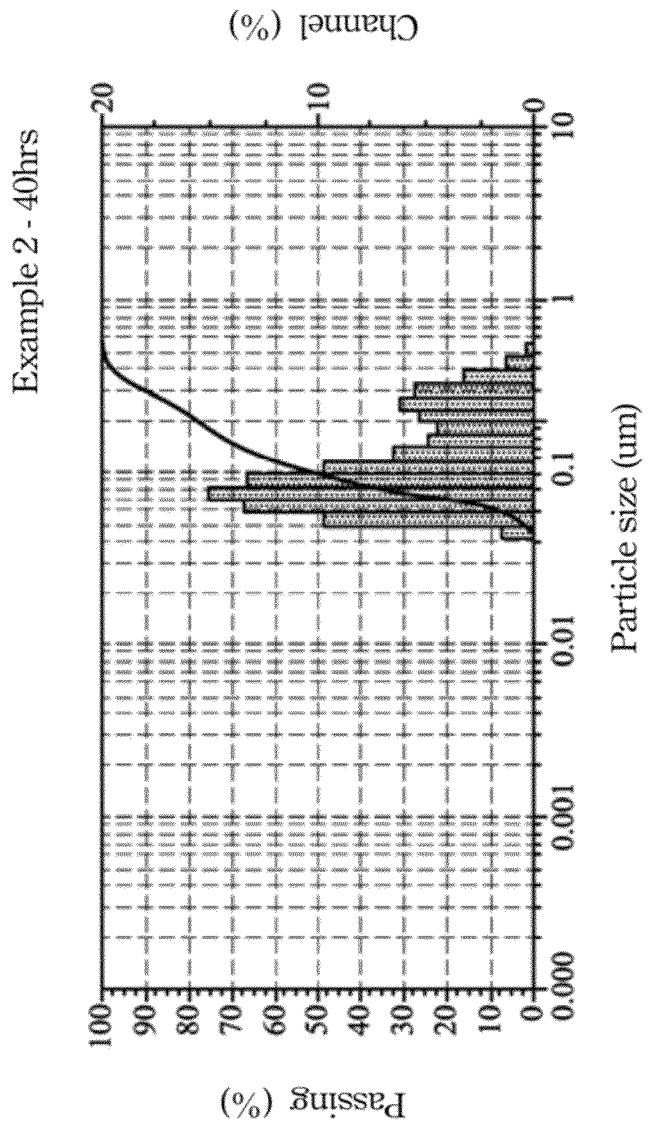
Figure 1E:
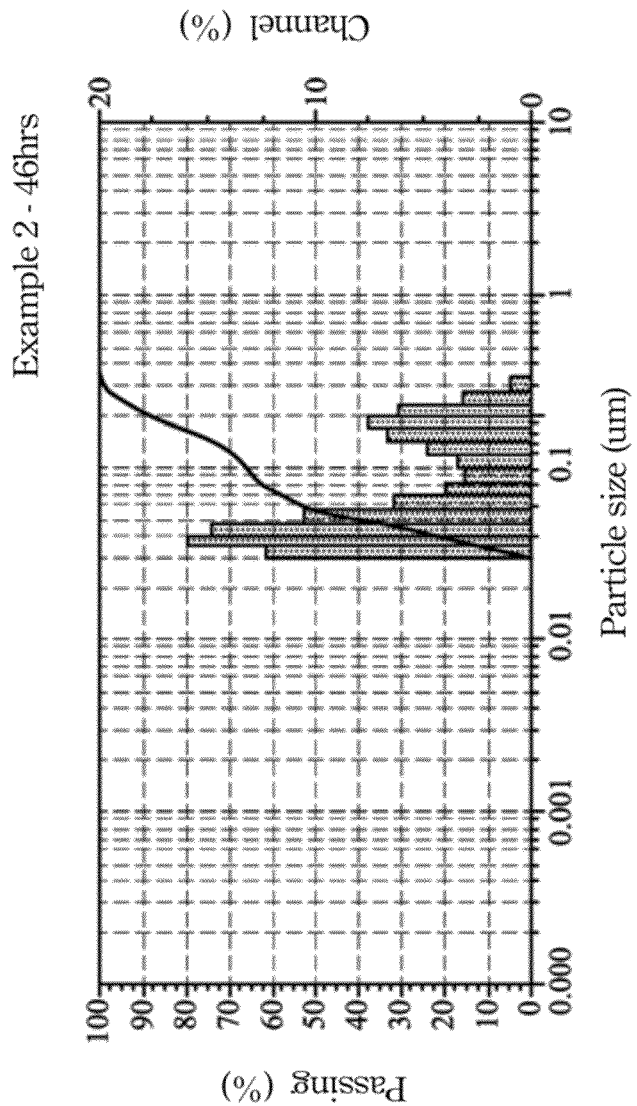
Figure 1F:
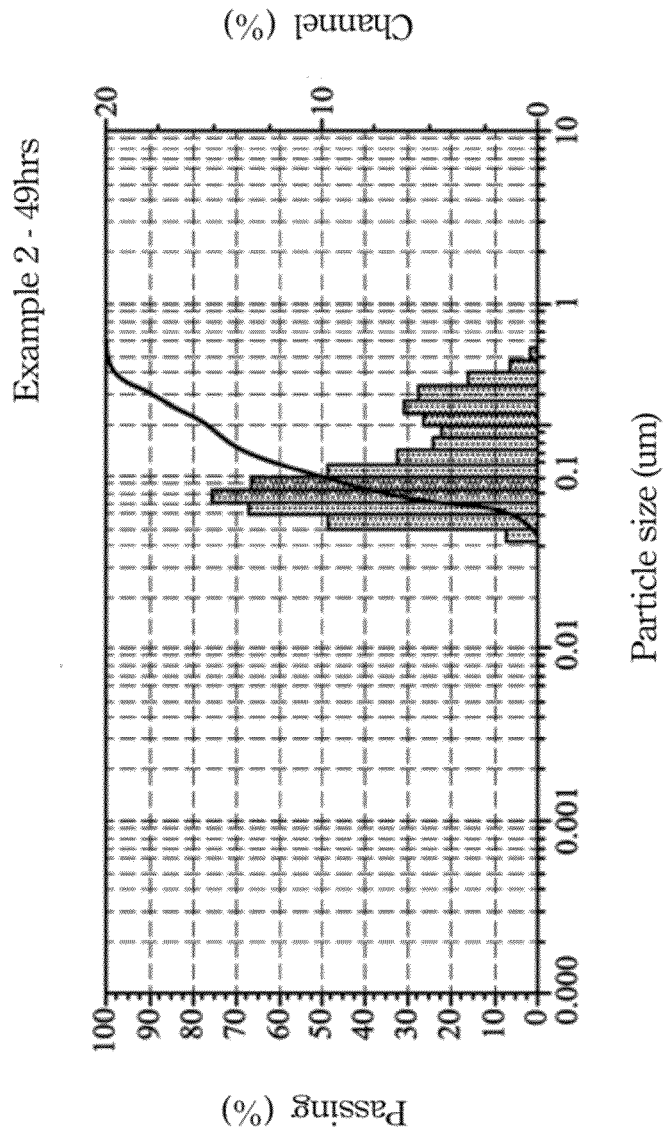

Accordingly, this invention provides a method for preparing nano silver particles with a size of 50 nm to 120 nm. In the following detailed description, for purposes of explanation, numerous specific details are set forth in order to provide a thorough understanding of the disclosed embodiments. It will be to apparent, however, that one or more embodiments may be practiced without these specific details. In other instances, well-known structures and devices are schematically shown in order to simplify the drawing.

The method comprises mixing polyvinyl pyrrolidone (PVP) and silver nitrate ($AgNO_3$) in a solvent to form a reactive solution, heating the reactive solution to a temperature less than the boiling point of the solvent for the formation reaction of nano silver particles, adding an accelerating agent into the reactive solution during the formation reaction of the nano silver particles, and terminating the formation reaction when the size of the nano silver particles formed in the reaction solution reaches about 50 nm to 120 nm. Aspects of the method will be described in greater detail below.

First, polyvinyl pyrrolidone (PVP) and silver nitrate ($AgNO_3$) are mixed in a solvent to form a reactive solution and the molar ratio of the PVP to the solvent is 0.012 to 0.032 and the molar ratio of the $AgNO_3$ to the PVP is 0.5 to 1.5. According to an embodiment of the invention, the solvent is selected from the group consisting of isopropyl alcohol (IPA), $H_2O$ and a combination thereof.

Secondly, the reactive solution is heated to a temperature less than the boiling point of the solvent for the formation reaction of nano silver particles. According to another embodiment of the invention, the temperature is in a range of 60° C. to 80° C., preferably in 65° C. to 78° C.

Subsequently, an accelerating agent is added into the reactive solution during the formation reaction of the nano silver particles. According to an embodiment of the invention, the accelerating agent is glucose which is added into the reactive solution after the reactive solution is heated for 20 hours. According to another embodiment, the accelerating agent is Hydrogen ($H_2$). If the accelerating agent is not $H_2$, the weight ratio of the accelerating agent to the reactive solution is about 0.01-2:97-99 (w/w). In the embodiment where the accelerating agent is $H_2$, $H_2$ is added into the reactive solution before the reactive solution is heated and the addition of $H_2$ into the reactive solution is discontinued after the reactive solution is heated for 6 hours to 20 hours, preferably 7.5 hours to 16 hours.

Finally, the formation reaction is terminated when the size of the nano silver particles formed in the reaction solution reaches about 50 nm to 120 nm. According to an embodiment, the reaction solution is cooled to room temperature after discontinuing to add $H_2$ into the reactive solution and stirred for another 10 hours to 20 hours.

Some embodiments are provided below to further illustrate this invention, but this invention is not limited thereto.

Comparative Example 1

(1) The manufacturing method of Comparative Example 1

The steps involved in the preparation of Comparative Example 1 are now described. First, PVP (MW 55000, commercial code CAS9003-39-8-85656-8, from Sigma-Aldrich, US) and $AgNO_3$ (purity 97%, commercial code CAS7761-88-82169-03, from Mallinckrodt Chemicals, US) were mixed in IPA (commercial code CMOS111-00000-72EC, from Echo Chemical Co., Ltd., Taiwan) to form a reactive solution. Next, the reactive solution was heated to 70° C. for the formation of nano silver particles. When the temperature thereof reached 70° C., the reaction time was monitored. Finally, the reactive solution was sampled after reaction times of 12 hrs, 21.5 hrs, 84 hrs and 90 hrs. The detailed manufacturing conditions are listed in Table 1.

TABLE 1

Detailed manufacturing conditions of Comparative Example 1.

| | |
|---|---|
| IPA | 500 g |
| PVP | 10 g |
| $AgNO_3$ | 8 g |
| Accelerating agent | None |
| Reactive Temperature | 70° C. |

TABLE 1-continued

Detailed manufacturing conditions of Comparative Example 1.

| | | | | |
|---|---|---|---|---|
| Stirring speed | 350 rpm | | | |
| Gas | $N_2$ | | | |
| Temperature control | Electronic temperature control | | | |
| Reaction time (Sampling time) | 12 hrs | 21.5 hrs | 84 hrs | 90 hrs |
| Average particle size of nano silver particles | 25 nm | 25 nm | 32 nm | 33 nm |

Example 1

(1) The manufacturing method of Example 1

The steps involved in the preparation of Example 1 are the same as those of Comparative Example 1, except that glucose as an accelerating agent was added into the reactive solution after a reaction time of 20 hrs. Next, the reactive solution was sampled after a reaction time of 28 hrs.

TABLE 2

Detailed manufacturing conditions of Example 1.

| | |
|---|---|
| IPA | 740.5 g |
| PVP | 4.5 g |
| $AgNO_3$ | 4.5 g |
| Accelerating agent | Glucose 5 g |
| Reactive Temperature | 70° C. |
| Stirring speed | 350 rpm |
| Gas | Air |
| Temperature control | Electronic temperature control |
| Reaction time (Sampling time) | 28 hrs |
| Average particle size of nano silver particles | 57 nm |

Example 2

(1) The manufacturing method of Example 2

The steps involved in the preparation of Example 2 are now described. First, PVP (MW 55000, commercial code CAS9003-39-8-85656-8, from Sigma-Aldrich, US) and $AgNO_3$ (purity 97%, commercial code CAS7761-88-82169-03, from Mallinckrodt Chemicals, US) were mixed in IPA (commercial code CMOS111-00000-72EC, from Echo Chemical Co., Ltd., Taiwan) to form a reactive solution. Secondly, NaOH (commercial code CAS1310-73-2, from Sigma-Aldrich, US) as the accelerating agent was added into the reaction solution when the temperature thereof reached to 76.5° C. Next, the reactive solution was sampled after reaction times of 18 hrs, 26 hrs, 40 hrs, 46 hrs and 49 hrs. The detailed manufacturing conditions of Example 2 are listed in Table 3.

TABLE 3

Detailed manufacturing conditions of Example 2.

| | | | | | |
|---|---|---|---|---|---|
| IPA | 500 g | | | | |
| PVP | 10 g | | | | |
| $AgNO_3$ | 8 g | | | | |
| Accelerating agent | Saturated NaOH solution 2 ml | | | | |
| Reactive Temperature | 76.5° C. | | | | |
| Stirring speed | 350 rpm | | | | |
| Gas | Air | | | | |
| Temperature control | Electronic temperature control | | | | |
| Reaction time (Sampling time) | 18 hrs | 26 hrs | 40 hrs | 46 hrs | 49 Hrs |

TABLE 3-continued

Detailed manufacturing conditions of Example 2.

| | | | | | |
|---|---|---|---|---|---|
| Average particle size of nano silver particles | 39 nm | 57 nm | 65 nm | 61 nm | 99 nm |

(2) The UV-Vis Spectrum of the Reactive Solution of Example 2

FIG. 1a shows the UV-Vis spectrum of the reactive solution of Example 2 after a reaction time of 26 hrs, and it shows a peak at 418 nm. It is known that nano silver particles absorb a specific wavelength between 410 nm to 435 nm, and therefore, the peak at 418 nm in FIG. 1a indicates that nano silver particles have been formed in the reactive solution.

(3) The Particle Size Distribution Curve of the Reactive Solution of Example 2

FIG. 1b to FIG. 1g show particle size distribution curves of the silver nano particles formed after reaction times of 18 hrs, 26 hrs, 40 hrs, 46 hrs and 49 hrs.

(4) The Color of the Reactive Solution of Example 2

It is known that the color of a nano silver particle solution is different when the concentration of the solution has been changed. In the beginning, the color of the reactive solution of Example 2 is light brown and then turns to a normal shade of brown. After the reaction time, the color of the reactive solution turns red-brown and ultimately becomes blue-brown.

Example 3

(1) The Manufacturing Method of Example 3

The steps involved in the preparation of Example 3 are the same as those of Example 2, except that hydrogen as an accelerating agent was added into the reactive solution after a reaction time of 2 hrs. Next, the reactive solution was sampled after reaction times of 2 hrs and 7 hrs (hydrogen was added for 5 hrs). The detailed manufacturing conditions of Example 3 are listed in Table 4.

TABLE 4

Detailed manufacturing conditions of Example 3.

| | | |
|---|---|---|
| IPA | 500 g | |
| PVP | 7.5 g | |
| AgNO$_3$ | 8 g | |
| Accelerating agent | Hydrogen | |
| Reactive Temperature | 76.5° C. | |
| Stirring speed | 350 rpm | |
| Gas | Air | |
| Temperature control | Electronic temperature control | |
| Reaction time (Sampling time) | 2 hrs | 7 hrs |
| Average particle size of nano silver particles | 16 nm | 78 nm |

(2) The UV-Vis Spectrum of the Reactive Solution of Example 3

Figure 2A:
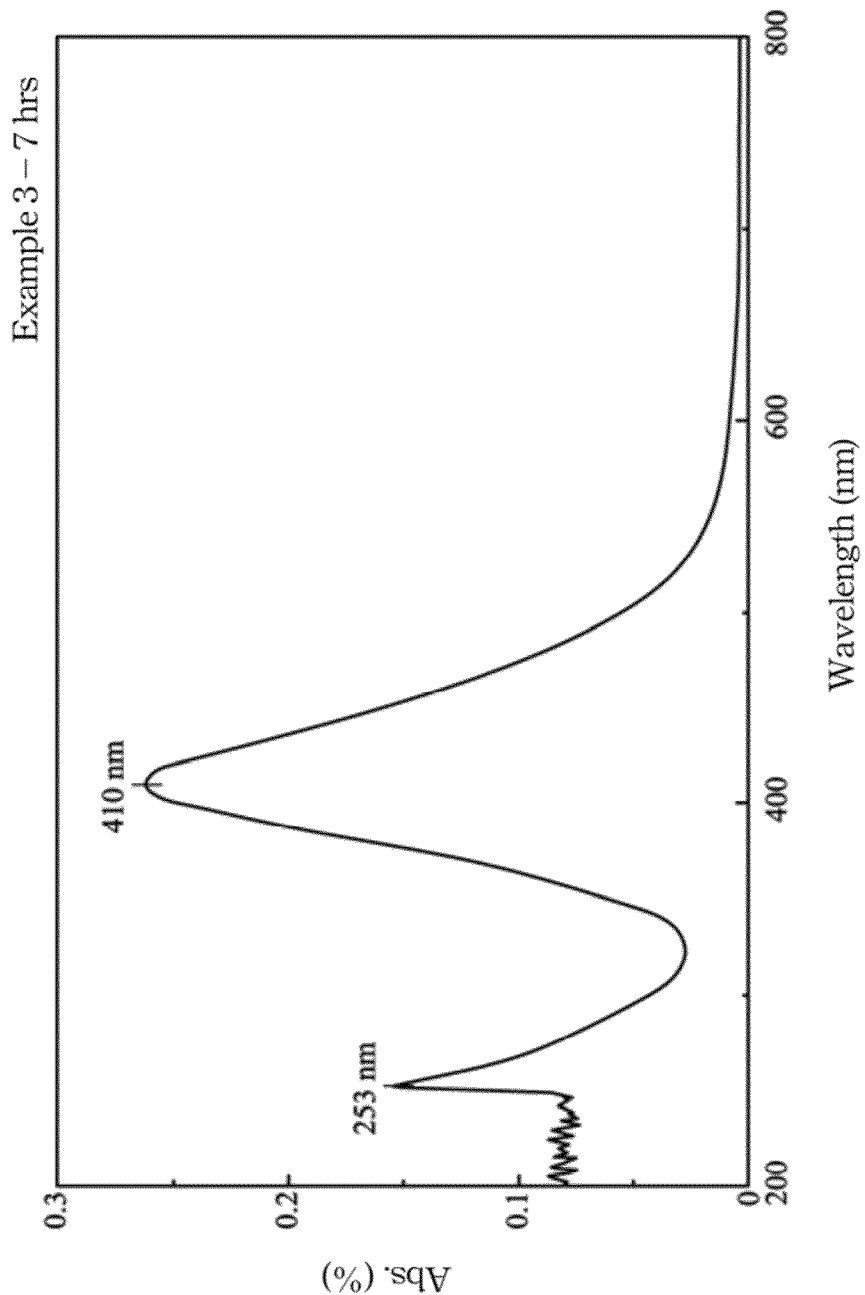
FIG. 2a is the UV-Vis spectrum of a reactive solution of Example 3 after a reaction time of 7 hours.

FIG. 2a shows the UV-Vis spectrum of the reactive solution of Example 3 after a reaction time of 7 hrs and it shows a peak at 410 nm in the spectrum.

(3) The Particle Size Distribution Curve of the Reactive Solution of Example 3

Figure 2B:
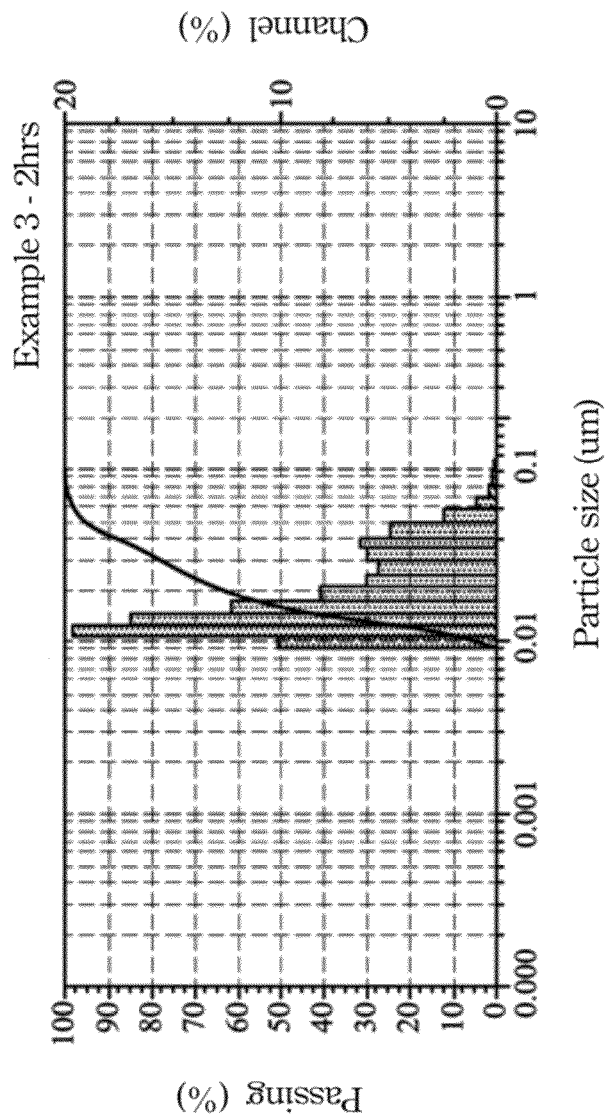
FIGS. 2b and 2c are nano silver particle size distribution curves of the reactive solution of Example 3 after reaction times of 2 hrs and 7 hrs.
Figure 2C:
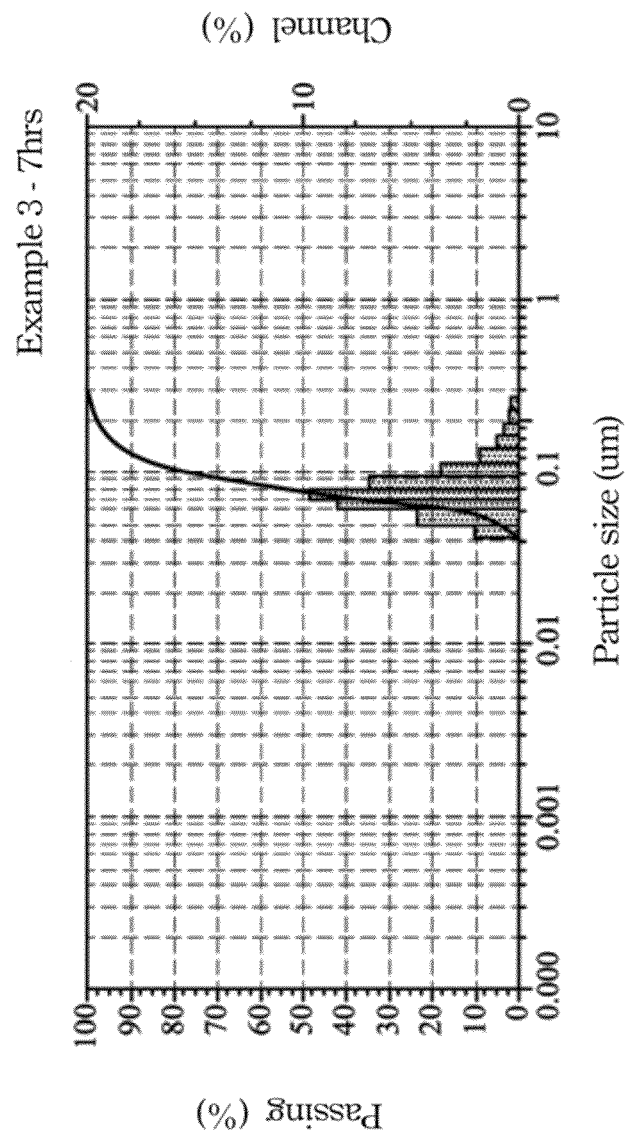

FIG. 2b and FIG. 2c show particle size distribution curves of nano silver particles formed after reaction times of 2 hrs and 7 hrs.

Example 4

(1) The Manufacturing Method of Example 4

The steps involved in the preparation of Example 4 are now described. First, PVP (MW 55000, commercial code CAS9003-39-8-85656-8, from Sigma-Aldrich, US) and AgNO$_3$ (purity 97%, commercial code CAS7761-88-82169-03, from Mallinckrodt Chemicals, US) were mixed in IPA (commercial code CMOS111-00000-72EC, from Echo Chemical Co., Ltd., Taiwan) to form a reactive solution. Secondly, H$_2$ was added into the reactive solution before the reactive solution was heated. Subsequently, the reactive solution was heated to 76.5° C. Next, the addition of H$_2$ into the reactive solution was discontinued after the reactive solution was heated for 7.5 hours and stirred at 76.5° C. for another 15 hrs. Finally, the reactive solution was sampled after a reaction time of 22.5 hrs. The detailed manufacturing conditions of Example 4 are listed in Table 5.

TABLE 5

Detailed manufacturing conditions of Example 4.

| | |
|---|---|
| IPA | 500 g |
| PVP | 7.5 g |
| AgNO$_3$ | 8 g |
| Accelerating agent | Hydrogen |
| Reactive Temperature | 76.5° C. |
| Stirring speed | 350 rpm |
| Gas | Air |
| Temperature control | Electronic temperature control |
| Reaction time (Sampling time) | 22.5 hrs = 7.5 hrs + 15 hrs |
| Average particle size of nano silver particle | 40 nm-150 nm |

(2) The UV-Vis Spectrum of the Reactive Solution of Example 4

Figure 3A:
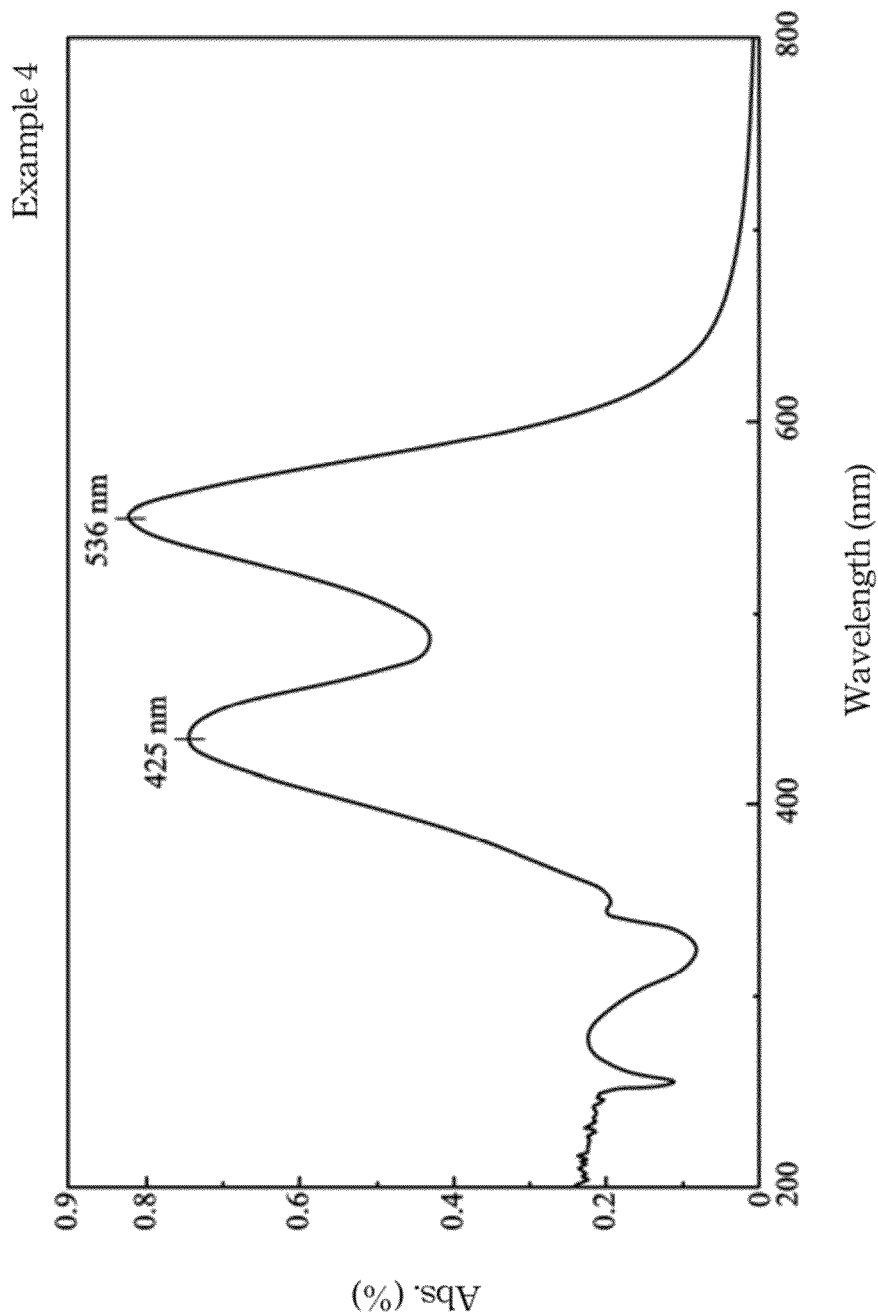
FIG. 3a is the UV-Vis spectrum of a reactive solution of Example 4 after a reaction time of 22.5 hrs.

FIG. 3a shows the UV-Vis spectrum of the reactive solution of Example 4 and it shows two peaks at 425 nm and 538 nm in the spectrum. These peaks are red-shift on the regular peak of nano silver particles, and resulted from the formation of nano silver particles of a larger size or the aggregation of nano silver particles in the reactive solution.

(3) The Particle Size Distribution Curve of the Reactive Solution of Example 4

Figure 3B:
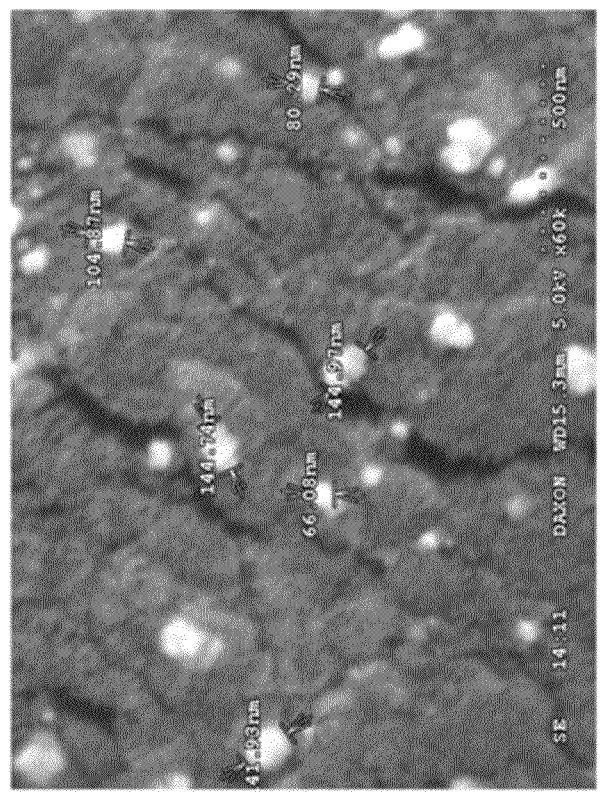
FIG. 3b is an image obtained by scanning electron microscopy of Example 4.

FIG. 3b shows that the nano silver particle size ranged from 40 nm to 150 nm.

(4) The Color of the Reactive Solution of Example 4

The color of the nano silver particle solution was observed as pink.

Example 5

(1) The Manufacturing Method of Example 5

The steps involved in the preparation of Example 5 are the same as those of Example 4, except the reactive solution was cooled to room temperature after the addition of $H_2$ to the reactive solution was discontinued and stirred at room temperature for another 12 hrs. Next, the reactive solution was sampled after a reactive time of 19.5 hrs. The detailed manufacturing conditions of Example 5 are listed in Table 6.

TABLE 6

Detailed manufacturing conditions of Example 5.

| | |
|---|---|
| IPA | 500 g |
| PVP | 7.5 g |
| AgNO$_3$ | 8 g |
| Accelerating agent | Hydrogen |
| Reactive Temperature | 76.5° C. |
| Stirring speed | 350 rpm |
| Gas | Air |
| Temperature control | Electronic temperature control |
| Reaction time (Sampling time) | 19.5 hrs = 7.5 hrs + 12 hrs |
| Average particle size of nano silver particle | 52 nm |

(2) The UV-Vis Spectrum of the Reactive Solution of Example 5

Figure 4:
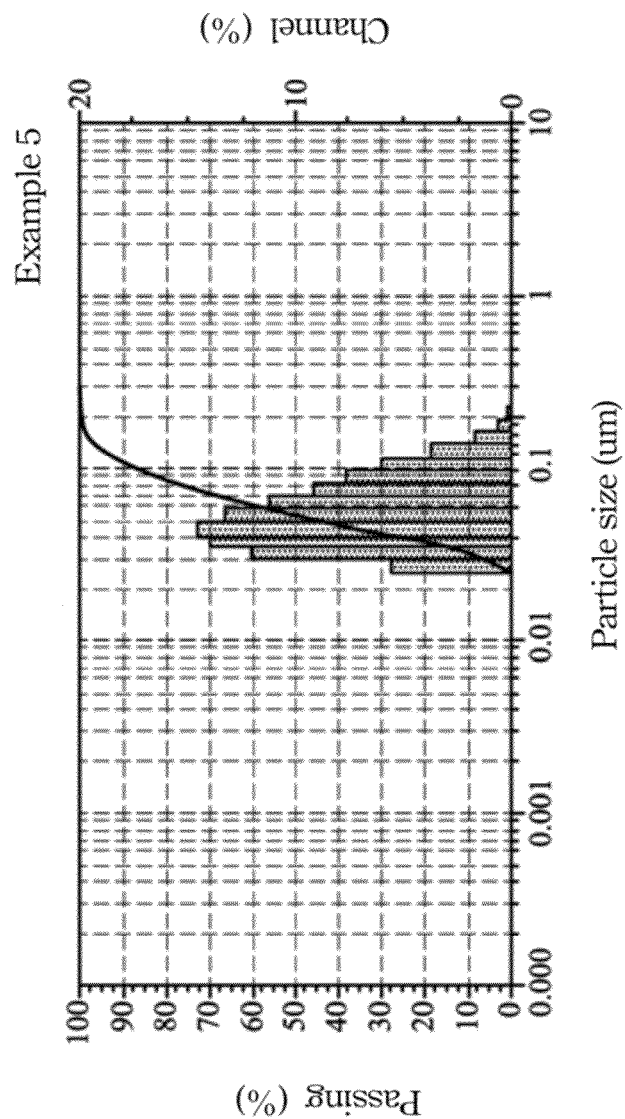
FIG. 4 illustrates nano silver particle size distribution curves of a reactive solution of Example 5 after a reaction time of 19.5 hrs.

FIG. 4 is the UV-Vis spectrum of the reactive solution of Example 5.

(3) The Color of the Reactive Solution of Example 5

The color of the reactive resolution of Example 5 was observed as yellow-brown.

Example 6

(1) The Manufacturing Method of Example 6

The steps involved in the preparation of Example 6 are now described. First, PVP (MW 55000, commercial code CAS9003-39-8-85656-8, from Sigma-Aldrich, US) and AgNO$_3$ (purity 97%, commercial code CAS7761-88-82169-03, from Mallinckrodt Chemicals, US) were mixed in $H_2O$ to form a reactive solution. Secondly, $H_2$ was added into the reactive solution before the reactive solution was heated. Next, the reactive solution was heated to 80° C. When the reactive solution was heated for 16 hrs, nano silver particles formed in the reactive solution with a particle size of 70 nm to 110 nm. The detailed manufacturing conditions of Example 6 are listed in Table 7.

TABLE 7

Detailed manufacturing conditions of Example 6.

| | |
|---|---|
| H$_2$O | 500 g |
| PVP | 8 g |
| AgNO$_3$ | 8 g |
| Accelerating agent | Hydrogen |
| Reactive Temperature | 80° C. |
| Stirring speed | 350 rpm |
| Gas | H$_2$ |
| Temperature control | Electronic temperature control |
| Reaction time (Sampling time) | 16 hrs |
| Average particle size of nano silver particle | 70 nm-110 nm |

Example 7

The manufacturing steps of Example 7 are the same as those of Example 6, except that PVP was 12 g and the reaction time was 10 hours. Nano silver particles formed in the reactive solution with a particle size of 60 nm to 120 nm.

TABLE 8

The detailed manufacturing conditions of Example 7.

| | |
|---|---|
| H$_2$O | 500 g |
| PVP | 12 g |
| AgNO$_3$ | 8 g |
| Accelerating agent | Hydrogen |
| Reactive Temperature | 80° C. |
| Stirring speed | 350 rpm |
| Gas | H$_2$ |
| Temperature control | Electronic temperature control |
| Reaction time (Sampling time) | 10 hrs |
| Average particle size of nano silver particle | 60 nm-120 nm |

Example 8

The manufacturing steps of Example 8 are the same as those of Example 7, except that the PVP was 8 g. Nano silver particles formed in the reactive solution with a particle size of 60 nm to 100 nm.

TABLE 9

The detailed manufacturing conditions of Example 8.

| | |
|---|---|
| H$_2$O | 500 g |
| PVP | 8 g |
| AgNO$_3$ | 8 g |
| Accelerating agent | Hydrogen |
| Reactive Temperature | 80° C. |
| Stirring speed | 350 rpm |
| Gas | H$_2$ |
| Temperature control | Electronic temperature control |
| Reaction time (Sampling time) | 10 hrs |
| Average particle size of nano silver particle | 60 nm-100 nm |

While the invention has been described by way of example(s) and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for preparing nano silver particles comprising the steps of:
mixing polyvinyl pyrrolidone (PVP) and silver nitrate (AgNO$_3$) in a solvent to form a reactive solution, wherein the solvent is selected from the group consisting of isopropyl alcohol (IPA), H$_2$O and a combination thereof;
heating the reactive solution to a temperature less than the boiling point of the solvent for the formation reaction of nano silver panicles;
adding an accelerating agent into the reactive solution during the formation reaction of the nano silver particles; and
terminating the formation reaction when the size of the nano silver particles formed in the reaction solution reaches about 50 nm to 120 nm.

2. The method of claim 1, wherein the molar ratio of the PVP to the solvent is 0.012 to 0.032 and the molar ratio of the AgNO$_3$ to the PVP is 0.5 to 1.5.

3. The method of claim 1, wherein the temperature is in a range of 60° C. to 80° C.

4. The method of claim 1, wherein the reaction time for formation of the nano silver particles is from 5 hours to 50 hours.

5. The method of claim 1, wherein the accelerating agent is selected from the group consisting of glucose, amine, Sodium hydroxide (NaOH), Potassium hydroxide (KOH), Hydrogen ($H_2$) and a combination thereof.

6. A method for preparing nano silver particles comprising the steps of:
   mixing polyvinyl pyrrolidone (PVP) and silver nitrate ($AgNO_3$) in a solvent to form a reactive solution;
   heating the reactive solution to a temperature less than the boiling point of the solvent in the presence of hydrogen ($H_2$) for the formation reaction of nano silver particles; and
   terminating the formation reaction when the size of the nano silver particles formed in the reaction solution reaches about 50 nm to 120 nm.

7. The method of claim 6, wherein the solvent is selected from the group consisting of isopropyl alcohol (IPA), $H_2O$ and a combination thereof.

8. The method of claim 6, wherein the temperature is in a range of 60° C. to 80° C.

9. The method of claim 6, wherein heating the reactive solution to the temperature less than the boiling point of the solvent in the presence of hydrogen comprises:
   adding the hydrogen into the reactive solution;
   heating the reactive solution for 6 to 20 hours; and
   discontinuing the addition of the hydrogen.

10. The method of claim 9, wherein heating the reactive solution to the temperature less than the boiling point of the solvent in the presence of hydrogen, after discontinuing the addition of the hydrogen, further comprises:
    cooling the reactive solution to a room temperature; and
    stirring the reactive solution for another 10 to 20 hours, after the reactive solution is cooled to the room temperature.

* * * * *